United States Patent [19]

Williams

[11] 4,177,318

[45] Dec. 4, 1979

[54] SPECTROSCOPY

[75] Inventor: Ernald V. Williams, Llanelli, Wales

[73] Assignee: British Steel Corporation, London, England

[21] Appl. No.: 818,712

[22] Filed: Jul. 25, 1977

[30] Foreign Application Priority Data

Aug. 2, 1976 [GB] United Kingdom .............. 32120/76
Aug. 13, 1976 [GB] United Kingdom .............. 33811/76

[51] Int. Cl.$^2$ .......................... B32B 9/04; B05B 5/12
[52] U.S. Cl. .................................. 428/408; 428/539; 427/113; 427/399; 427/126
[58] Field of Search .............. 427/113, 122, 126, 399; 428/408, 539

[56] References Cited

U.S. PATENT DOCUMENTS 3,342,627 9/1967 Paxton ................................. 427/113
3,939,028 2/1976 Schiffarth ............................ 427/113

Primary Examiner—Michael F. Esposito
Attorney, Agent, or Firm—Bacon & Thomas

[57] ABSTRACT

A graphite electrode for use in spectroscopic analysis in which at least the region of the electrode intended for contact with the material to be analyzed has a layer comprising the heat reaction product of graphite with a salt of a refractory metal and a salt of an alkali earth metal.

16 Claims, No Drawings

SPECTROSCOPY

This invention relates to graphite electrodes for spectroscopic analysis and is particularly, although not exclusively, concerned with graphite furnace tubes for use in the detection of metals by atomic absorption spectrometry. The present invention is particularly concerned with furnace tubes which are used in analysing the metal content in canned foods by atomic absorption spectrometry; the lead content in particular is extremely deleterious to the graphite furnace tubes and in analyses involving high acid concentrations, for example those containing up to 40 percent $HNO^3$ by volume, the useful campaign life of a graphite furnace tube is limited to 25–30 atomisations. Even with this limited life, a considerable variation in accuracy is found to exist between atomisations.

According to one aspect of the present invention, a graphite electrode for use in spectroscopic analysis includes a region having a layer comprising the reaction product of graphite with a salt of a refractory metal and a salt of an alkali earth metal.

According to a further aspect of the present invention, a graphite electrode for use in spectroscopic analysis includes a region having a protective layer incorporating the carbide and/or nitride of a refractory metal with an alkali earth metal.

According to yet a further aspect of the present invention, a method for producing a graphite electrode for spectroscopic analysis comprises treating a region of the electrode with a salt of a refractory metal together with a salt of an alkali earth metal and heating the treated graphite to a temperature producing reaction with the salts.

The region of the electrode which must be treated will be that coming into contact with the material to be analysed.

In a preferred embodiment of the invention, the alkali metal is calcium and is conveniently applied to the graphite electrode in the form of calcium carbonate in nitric acid. The refractory metal salt suitably is zirconium, conveniently in the form of zirconium nitrate.

An embodiment of the invention will now be described by way of example. In this example a graphite furnace tube for the analysis of lead in canned foods by atomic absorption spectroscopy is treated to improve life and accuracy. The treatment comprises soaking the interior of the graphite tube with a solution containing zirconium and calcium salts in the form of zirconium nitrate and calcium carbonate dissolved in nitric acid. A typical solution is produced by dissolving 1 gramme of zirconium nitrate and 0.1 grammes of calcium carbonate in 10 percent v/v of nitric acid to make 10 mls of solution.

The solution is applied to the interior of the furnace tube by way of a lining of an absorbent material such as filter paper which is subsequently soaked with 50μ of the treatment solution. A period of time, for example of the order of 5 minutes, is allowed to elapse to permit the solution to permeate from the absorbent layer into the adjacent graphite surface.

After the removal of the absorbent layer the tube is thermally treated by initial heating to a temperature effective to expel water and subsequently to permit reaction between the residual salts and the graphite in which the salts are absorbed.

Tests have indicated that an increase in useful life and accuracy can be obtained with salts of alkali earth metals and salts of refractory metals other than those exemplified. With substantially the same process route detailed in the example, graphite electrodes may be treated with any suitable combination of salts of zirconium, vanadium, molybdenum or lanthanum as representative of refractory metals or with magnesium as representative of alkali earth metals.

The heating may be achieved by passing an electric current through the tube or by other conventional means. A typical heating cycle comprises maintaining the tube at an initial temperature of 100° C. or above to produce drying and at a subsequent temperature of 1200° C. to 1250° C. to produce reaction between the salts and the graphite. It is believed that the reaction temperature produces a calcium-stabilised protective layer of zirconium carbides and nitrides within the tube and that these increase useful life and accuracy.

I claim:

1. A graphite electrode for use in spectrospopic analysis in which at least the region of the electrode intended for contact with the material to be analysed has a layer comprising the heat reaction product of graphite with a salt of a refractory metal selected from the group consisting of zirconium vanadium, molybdenum, and lanthanum and a salt of an alkali earth metal.

2. A graphite electrode as claimed in claim 1 wherein the reaction product includes a carbide/nitride of the refractory metal.

3. A graphite electrode as claimed in claim 1 wherein the alkali earth metal is calcium or magnesium.

4. A graphite electrode as claimed in claim 3 wherein the salt of the alkali earth metal is a metal nitrate.

5. A graphite electrode as claimed in claim 4 wherein the salt is calcium nitrate.

6. A graphite electrode as claimed in claim 5 wherein the calcium nitrate is in the form of calcium carbonate in nitric acid.

7. A graphite electrode as claimed in claim 6, wherein the salt of the refractory metal is a metal nitrate.

8. A graphite electrode as claimed in claim 7 wherein the salt is zirconium nitrate.

9. A method for producing a graphite electrode for spectroscopic analysis comprising treating at least the region of the electrode intended for contact with the material to be analysed with the salt of a refractory metal selected from the group consisting of zirconium, vanadium, molybdenum and lanthanum and the salt of an alkali earth metal and heating the treated graphite to a temperature producing a reaction with the salt.

10. A method as claimed in claim 9 wherein the heating is in an inert ambient.

11. A method as claimed in claim 10 wherein the ambient contains a reducing component.

12. A method as claimed in claim 9 wherein heating is by electric current through the graphite.

13. A method as claimed in claim 9 wherein the salt of the refractory metal is a metal nitrate.

14. A method as claimed in claim 9 wherein the alkali earth metal is selected from the group including calcium and magnesium.

15. A method as claimed in claim 14 wherein the salt of the alkali earth metal is a metal nitrate.

16. A graphite electrode when produced by the method of claim 9.